United States Patent [19]

Fiala

[11] Patent Number: Plant 6,974

[45] Date of Patent: Aug. 8, 1989

[54] CRABAPPLE TREE NAMED RED SWAN

[75] Inventor: John L. Fiala, Medina, Ohio

[73] Assignee: Chas. Klehm & Son, South Barrington, Ill.

[21] Appl. No.: 214,649

[22] Filed: Jun. 30, 1988

[51] Int. Cl.[4] ..... A01H 5/00

[52] U.S. Cl. ..... Plt./34

[58] Field of Search ..... Plt./34

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An ornamental flowering crabapple tree named Red Swan, having a graceful and small weeping form to 10 feet in maturity, with heavily textured, disease resistant lanceolate leaves. The leaves change in fall to a gold color. Bright red fruit is borne abundantly. The flower buds and blossoms are pendulous, and the initially coral pink buds change to pure white before the blossoms open.

4 Drawing Sheets

The present invention comprises a new and distinct cultivar of crabapple tree, botanically known as Malus, and hereinafter referred to by the cultivar name Red Swan.

The new cultivar was discovered by the inventor in 1968, resulting from a controlled cross by the inventor in Medina, Ohio of seed parent Malus 'Molton Lava' with pollen parent [(Malus 'Red Jade'×Malus 'Lemoine')×*Malus toringoides*].

Asexual reproduction by applicant in Medina, Ohio in the form of softwood cuttings and summer chip budding has demonstrated that the combination of characteristics as herein disclosed for the new cultivar are firmly fixed and are retained through successive generations of asexual reproduction.

Red Swan has not been observed under all possible environmental conditions. The phenotype may vary significantly with variations in environment such as temperature, light intensity, day length, available soil moisture, soil nutrients and pH level.

The following observations, measurements, and comparisons describe trees grown at Klehm Nursery, Barrington, Ill., under conditions which approximate those generally used in commercial practice.

The following traits have been repeatedly observed and are determined to be basic characteristics of Red Swan, which, in combination, distinguish this crabapple tree as a new and distinct cultivar:

1. Red Swan has a graceful and small weeping form, reaching 10 feet in height at maturity.

2. Its heavily textured, disease resistant, medium green lanceolate leaves change to an attractive golden fall color.

3. It abundantly bears bright red fruit, 5/16 to ⅜" in diameter.

4. Its weeping leaves add to an overall pendulous character.

5. The pendulous flower buds and blossoms add a dainty weeping character in the spring flowering period.

6. Initially, the buds are coral pink, similar in size, habit, shape, and color to the just opening blossoms of *Halesia monticola* 'Rosea' blossoms. They then change to pure white; similar in size, habit, shape, and color to open *Malesia monticola* 'Rosea' blossoms.

Of the many commercial crabapple trees known to the inventor, the most similar in comparison to Red Swan is Red Jade. In comparison to Red Jade, Red Swan has more, and disease-resistant, foliage; daintier and more distinct bud color, habit and shape; a more gracefully pendulous appearance, and narrower, more lanceolate and pendulous foliage.

The accompanying color photographic drawings show typical characteristics of Red Swan, with colors being as true as possible with illustrations of this type.

Sheet 1 is a photograph of Red Swan in perspective view.

Sheet 2 shows a leafed branch of Red Swan with buds in varying stages of openness.

Sheet 3 shows a branch of Red Swan bearing mature pure white blossoms.

Sheet 4 is a perspective view of a tree of Red Swan in full fruit and showing a turning in color of the leaves.

In the following description, color references are made to The Royal Horticultural Society Colour Chart (RHS).

TREE

Origin: Seedling.

Parentage:

*Seed parent.*—Malus 'Molten Lava'.

*Pollen parent.*—(Malus 'Red Jade'×Malus 'Lemoine')×*Malus toringoides.*

Classification:

*Botanic.*—Malus×cv 'Red Swan'.

*Commercial.*—Ornamental flower crabapple.

Propagation: Chip budding, bench grafting or softwood cuttings.

Branches: Pendulous, delicate, fine.

Height: Approximately 10 feet at 15 years.

Growth habit: Weeping, pendulous.

Fruit bearing habit: Annual and abundant.

Foliage:

*Size of leaf.*—2.5" long by 1" wide.

*Shape of leaf.*—Lanceolate.

*Margin.*—Entire.

*Texture.*—Heavy.

FLOWERS

Buds:

*Color.*—Coral, pink 37B-C to white.

*Size.*—Small.

*Shape.*—Ovoid, then bell shaped.

Form: Clusters of 3 to 4.

Date of first bloom: Normally May 10–15.
Date of full bloom: Normally May 15–20.
Color: Mature, fully open, pure white blossoms.

FRUIT

Date of maturity: October 15.
Shape: Round, 5/16" to ⅜" in diameter.
Hardness: Firm.
Form: Clusters of 5 to 6.
Skin: Glossy.

Color: 44A-B.
Keeping quality: To about early December.
Insect and disease resistance: Excellent disease resistance to the five common crabapple diseases; apple scab, cedar-apple rust, fire blight, frog-eye leaf spot and powdery mildew.

I claim:

1. A new and unique flowering crabapple tree named Red Swan, as illustrated and described.

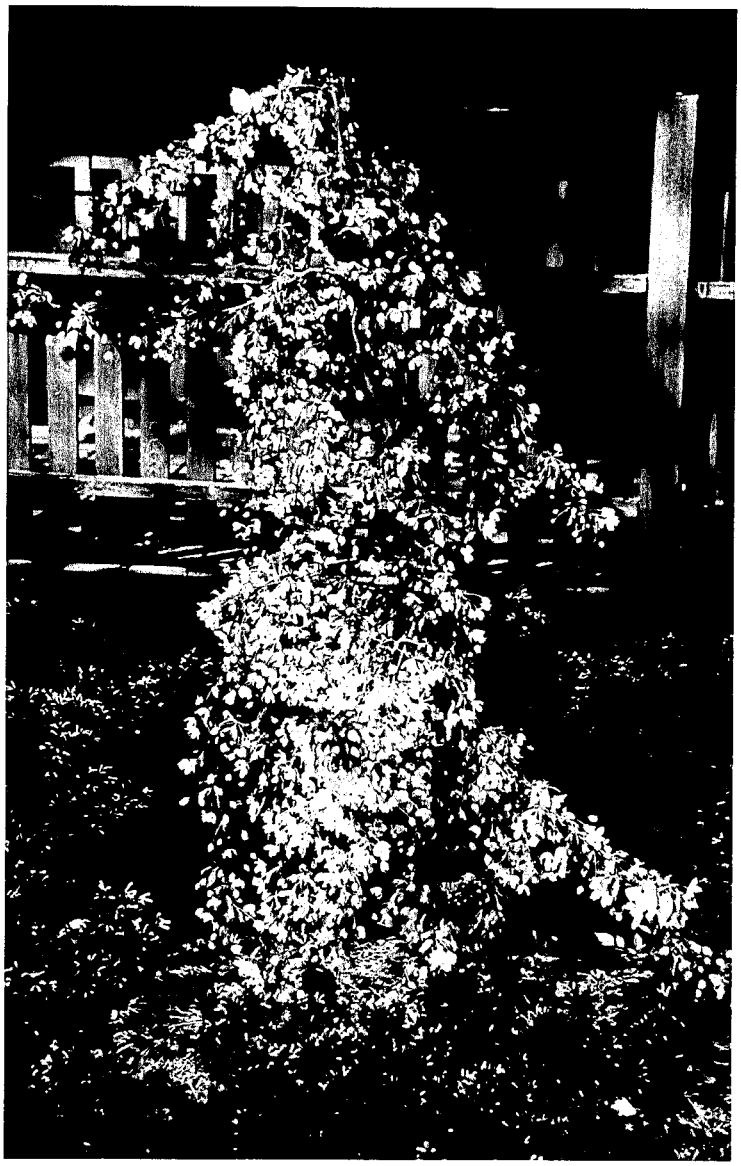

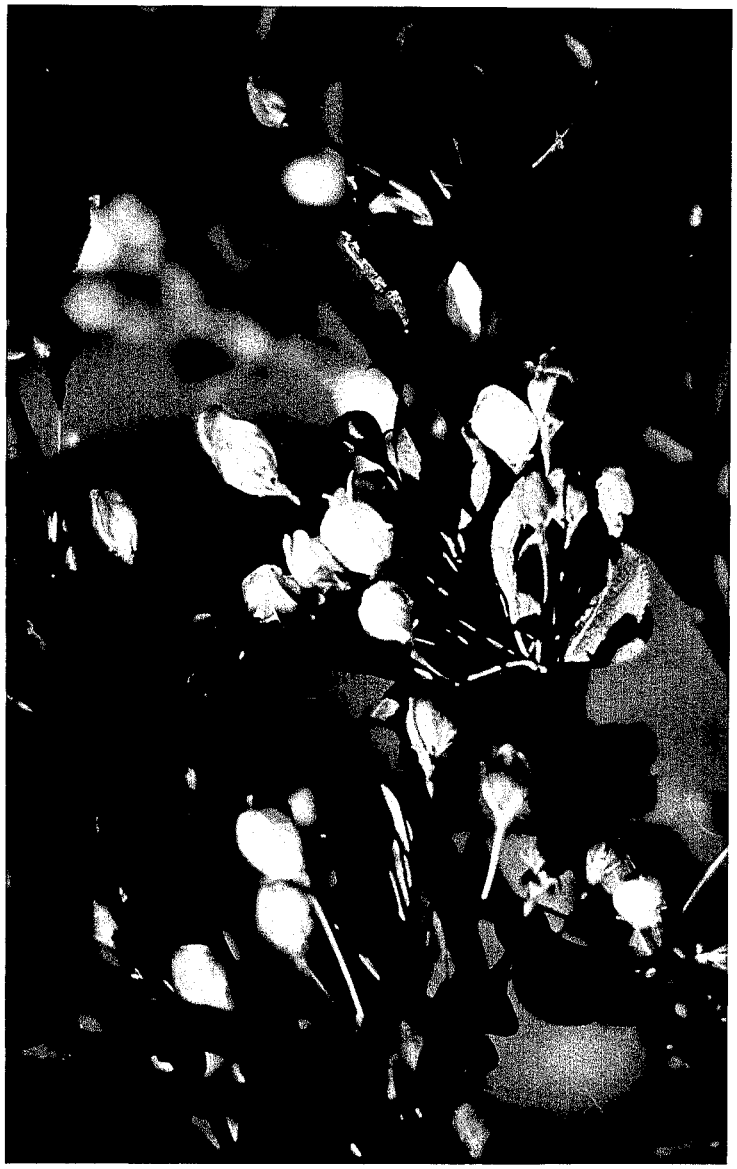

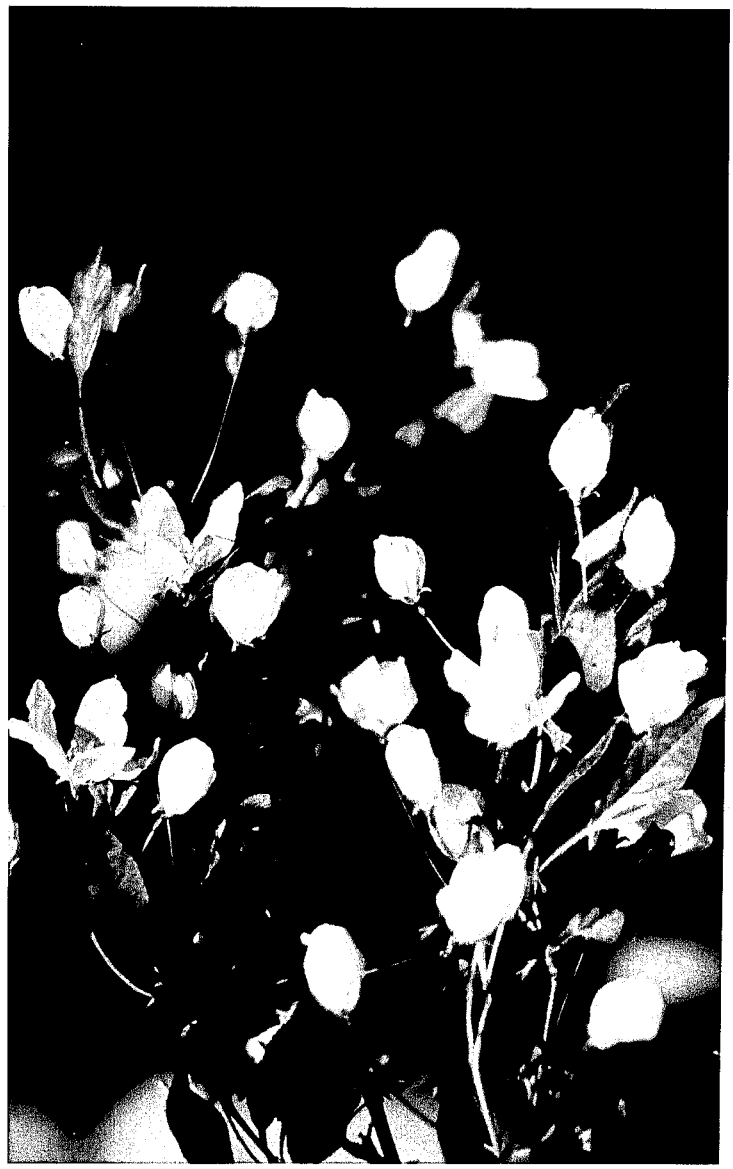

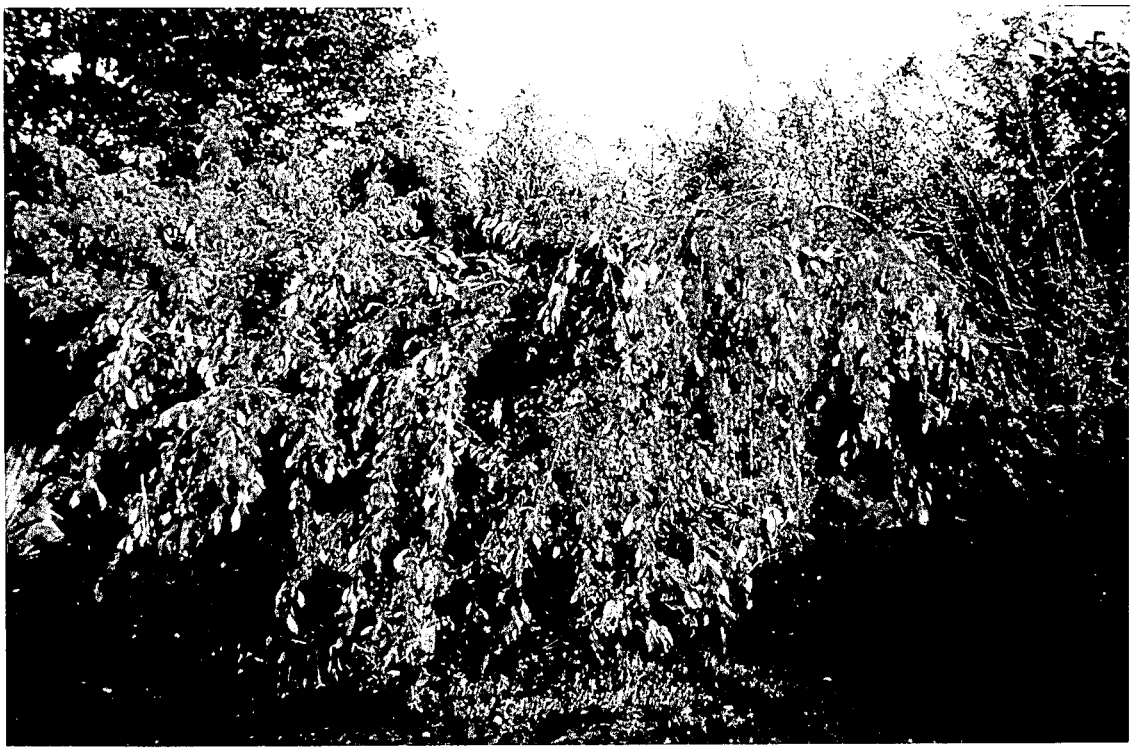

* * * * *